| United States Patent [19] | [11] Patent Number: 4,746,604 |
| --- | --- |
| Mowshowitz | [45] Date of Patent: May 24, 1988 |

[54] SPECIFIC BINDING ASSAYS UTILIZING A VIABLE CELL AS A LABEL

[75] Inventor: Solomon Mowshowitz, New York, N.Y.

[73] Assignee: Enzo Biochem, Inc., New York, N.Y.

[21] Appl. No.: 738,135

[22] Filed: May 24, 1985

[51] Int. Cl.$^4$ ............... G01N 33/53; G01N 33/554
[52] U.S. Cl. .................................. 435/7; 435/29; 435/34; 435/39; 435/177; 435/810; 435/881; 435/883; 436/519; 436/520; 436/802
[58] Field of Search ............ 435/5, 7, 177, 810, 435/881, 883, 29, 34, 39; 436/519, 520, 802, 819, 827, 829

[56] References Cited

U.S. PATENT DOCUMENTS

| 4,104,126 | 8/1978 | Young | 435/7 |
| 4,189,466 | 2/1980 | Ainis et al. | 435/7 |
| 4,223,005 | 9/1980 | Teodorescu et al. | 435/7 |

FOREIGN PATENT DOCUMENTS 0004189  9/1985  PCT Int'l Appl. .................. 435/7

OTHER PUBLICATIONS

American Heritage Dictionary, 2nd College Edition, p. 87, Houghton Mifflin Co., Boston, 1982.
Haimovich, J. of Immunology 97(3) pp. 338–343, (1966).

Primary Examiner—Robert J. Warden
Assistant Examiner—Robert Benson
Attorney, Agent, or Firm—Charles J. Herron

[57] ABSTRACT

A method and composition for detecting analyte moieties by means of a signalling moiety capable of aggrandizement are disclosed. The signalling moiety can be attached to or not attached to the analyte moiety/analyte-specific moiety complex. The signalling moiety can be viable or non-viable. The methods disclosed herein provide a sensitive assay for the detection of a wide range of different analyte moieties.

8 Claims, No Drawings

SPECIFIC BINDING ASSAYS UTILIZING A VIABLE CELL AS A LABEL

BACKGROUND OF THE INVENTION

This invention relates to a method for detecting analyte moieties by means of a signalling moiety, and particularly by means of a signalling moiety that can aggrandize or be aggrandized.

Assay systems for the detection of analyte moieties of biomedical interest have been known for a number of years. These systems include, for example, immunodiffusion, immunoelectrophoresis, agglutination, and immunofluorescence. These systems variously have limitations in convenience, sensitivity, ease of sample preparation, adaptability to automation, and applicability to various specific analyte moieties.

Radioimmunoassay (RIA) represents a convenient, sensitive, flexible, and easily automatable method for the detection. The disadvantages of RIA detection systems relates to the problems inherent in the use of radioisotopes, which provide the signal in RIA's. The problems include, variously, high cost and short storage life of the radiolabeled reagents, the requirement for special equipment for detection of the signal, the health hazard to laboratory personnel, and the expense and inconvenience of disposal of the radioactive waste.

Recently, a sensitive and convenient method for detection has been introduced, which does not require the use of radioisotopes. The enzyme-linked immunosorbent assay (ELISA) makes use of enzymes as signalling moieties. The sensitivity of ELISA is limited, in part, by the number of enzyme molecules that can be attached to the analyte-specific moiety used. When an analyte moiety is capable of growth (e.g. a bacterium), it is often advantageous to grow it, either in vivo or in vitro to make the task of detection easier. Following growth, the analyte moiety can be detected by means of observing any of its physical or metabolic characteristics for example, its cellular or colonial morphology, nutritional requirements, metabolic products, staining characteristics or potential for pathogenesis. As few as one viable bacterial cell can be detected in this way.

The ability of bacteria to grow has made them useful signalling moieties for the detection of other moieties. When the ability of the bacterium to grow is dependent upon the analyte moiety (e.g. when the bacteria are auxotrophic for the analyte moiety), the growth of the bacteria can be used to detect the presence of the analyte moiety. The growth of the bacteria is stoichiometrically related to the amount of analyte moiety present. Of course, this type of bioassay is limited to specific signalling moiety-analyte moiety pairs.

OBJECTS OF THE INVENTION

An object of this invention is to provide a method for detecting analyte moieties by means of a signalling moiety capable of aggrandizement (growth, replication, proliferation, elongation, or polymerization).

An additional object of this invention is to provide a sensitive method for the detection of analyte moieties.

Another object of this invention is to provide a method that may permit detection of one analyte moiety.

A further object of this invention is to provide a method which can detect the presence of an analyte moiety by means of a signalling moiety unattached to the analyte moiety/analyte-specific moiety complex that is able to aggrandize independent of the analyte moiety.

Another object of this invention is to provide a kit with which an analyte moiety can be detected by means of a signalling moiety capable of aggrandizement.

SUMMARY OF THE INVENTION

In accordance with this invention, there is provided a method for detecting an analyte moiety. The method comprises several embodiments. In a first embodiment, an analyte moiety is complexed to an analyte-specific moiety. If neither the analyte moiety nor the analyte-specific moiety is also a signalling moiety capable of aggrandizement, or if either one is capable of aggrandizement but this capability is not desired to be utilized, then a signalling moiety capable of aggrandizement is attached to either the analyte moiety or the analyte-specific moiety. The signalling moiety can be viable or non-viable.

In the second embodiment, the signalling moiety is not attached to the analyte moiety/analyte-specific moiety complex. The signalling moiety is dependent upon a nutrient for aggrandizement or for the ability to generate signal. The nutrient may be provided by means of a catalyst. If neither the analyte moiety nor the analyte-specific moiety is also a suitable catalyst, or if either one is a catalyst, but its use as a catalyst is not desired, then a catalyst is attached to either the analyte moiety or the analyte-specific moiety. The catalyst generates a nutrient from a precursor, which nutrient enables a viable signalling moiety to aggrandize or to generate a signal, or said catalyst generates free radicals which enable a non-viable signalling moiety to aggrandize. Alternatively, the nutrient may be provided to the viable signalling moiety by means of a carrier such as a liposome, containing the nutrient, attached to the analyte/analyte-specific moiety complex.

DETAILED DESCRIPTION OF THE INVENTION

I. Definitions

In this invention, the following defined terms are employed:

Analyte Moiety—An analyte moiety is the substance to be detected or quantified.

Analyte-Specific Moiety—This is a moiety capable of complexing to a particular analyte moiety by recognizing some informational portion of the analyte moiety.

Bridging Moiety—This is a moiety joining any two moieties.

Signalling Moiety-Specific Moiety—This is a moiety capable of complexing to a particular signalling moiety by recognizing some informational portion of the signalling moiety.

Signalling Moiety—This is the moiety which is detected by the user. It can be viable or non-viable.

Signal—This is what is detected in the assay. The presence of the signal indicates the presence of the signalling moiety.

Viable Signalling Moiety—A signalling moiety capable of growth, replication and/or proliferation. All these moieties comprise nucleic acid, and have the ability to produce copies of their nucleic acids independently or with the aid of a host.

Non-Viable Signalling Moiety—A signalling moiety capable of undergoing elongation or polymerization.

Analyte Moiety/Analyte-specific Moiety Complex—This is the entity formed when the analyte-specific moiety recognizes information of the analyte moiety and binds to the analyte moiety.

Signalling-Analyte-Entity—This term is used to denote the entity comprising at least an analyte moiety, an analyte-specific moiety and a signalling moiety. The signalling moiety can be the analyte moiety or the analyte-specific moiety.

Attached—A moiety is attached to another moiety if it is bound to it covalently (directly or indirectly) or non-covalently (directly or indirectly).

Direct Attachment—This occurs when a moiety is attached to another moiety without an intermediate moiety.

Indirect Attachment—This occurs when a moiety is attached to another moiety through an intermediate moiety.

Aggrandizement—This refers to the increase in mass, size, volume, number of molecular weight of the signalling moiety, and this increase can be the result of a signalling moiety becoming attached to other like or unlike moieties.

Independent Aggrandizement—The term means that the signalling moiety, if not also the analyte moiety, is not directly dependent on the analyte moiety itself for aggrandizement. The presence of the analyte moiety may, however, lead indirectly to the provision of a nutrient required by the signalling moiety for aggrandizement.

Information—This is the part of the analyte moiety that the analyte-specific moiety is capable of recognizing.

Recognition—This occurs when the analyte-specific moiety binds to the analyte moiety.

Nutrient—Any molecule required by the signalling moiety for aggrandizement or for generation of signal.

Precursor—A substance that is converted by a catalyst to a nutrient that can be utilized by a viable signalling moiety for aggrandizement or for generation of signal.

DETAILED DESCRIPTION OF THE INVENTION

A method is provided for detecting analyte moieties by forming a complex between an analyte moiety and an analyte-specific moiety and detecting the analyte moiety by means of a signalling moiety that is capable of independent aggrandizement. Independent aggrandizement means that the signalling moiety is not directly dependent on the analyte moiety itself for aggrandizement. In the formats in which the analyte moiety itself is the signalling moiety, each signalling moiety is not dependent on the presence of other analyte moieties for aggrandizement. The signalling moiety can be attached directly or indirectly or not attached at all to the analyte moiety/analyte-specific moiety complex. The various embodiments are discussed herein below.

Viable Signalling Moieties

Viable signalling moieties capable of aggrandizement are moieties that can grow, replicate, or proliferate in a suitable environment when supplied with the proper nutrients. The nutrients comprise all metabolic requirements of the signalling moiety and can include intact cells. The advantage of using a signalling moiety that can aggrandize is that it permits the generation of more signalling moieties thus providing for more signal. Viable signalling moieties include, for example, phages, viruses, bacteria, protozoa, ricketzia, fungi, yeast, algae, microorganisms, prokaryote cells, eukaroyote cells, tumor cells, plant cells, and animal cells. Preferred viable signalling moieties are phages, viruses, bacteria, and yeast. Particularly preferred are bacteria and yeast.

Viable signalling moieties can be detected by observing the actual moieties themselves or the metabolites produced by the moieties. Signalling moieties that are bacteria may themselves be observed by the presence, for example, of colonies on a solid nutrient plate or turbidity in a liquid medium. Bacteria that can grow under special conditions, (e.g., elevated temperatures or low pH) or that are readily distinguishable from other viable signalling moieties (e.g. they produce colonies with distinctive morphologies or colors) have an additional advantage in that they can be observed in the presence of other signalling moieties not able to grow under these conditions or that do not exhibit these distinctive characteristics. An example of a bacterial species which forms distinctive colonies is *Serratia marsescens*, which forms red colonies.

Viable signalling moieties produce metabolites which can be detected to verify the presence of the signalling moiety. They comprise most cellular or viral products and components. They include, for example, proteins, hormones, antibodies, enzymes, epitopes, antigens, polypeptides, peptides, amino acids, nucleic acids, polynucleotides, nucleotides, nucleosides, bases, carbohydrates, sugars, starches, lipids, fatty acid esters, glycerols, fatty acids, carbohydrates, glycoproteins, lipoproteins, vitamins, steroids, drugs, flavones, antibiotics, terpenes, purines and pyrimidines. Preferred metabolites are proteins, polynucleotides, and polysaccharides. Particularly preferred are epitopes, antigens, enzymes, and polynucoeotides. Enzymes include, for example, hydrolases, esterases, phosphatases, peroxidases, catatases, glycosidases, oxidoreductases, proteases, lipases, and nucleases. Particularly preferred are phosphatases, peroxidases and oxidoreductases.

Detection of a metabolite can be by various means. A metabolite can be detected by means of a physical property, or a chemical property. Physical properties include, for example, all characteristics such as fluorescence emmission, ultra-violet absorption, molecular weight, electrophoretic mobility, and chromotographic behavior. Chemical properties include, all charactëristics which enable the metabolite to react with, interact with, or bind to other substances. The chemical property can be one that permits conversion of the metabolite into a compound that can be detected, one that enables the metabolite to convert a substance into a detectable product, or one that permits the attachment of the metabolite to a detectable substance.

Examples of metabolites that can be detected by the above methods include cofactors by means of their uv spectrum, peptides by means of their retention times on HPLC, ribonucleotides by means of orcinol, carboxylic acids by means of pH indicators, nucleic acids by means of ethidium bromide, epitopes by means of antibodies attached to a fluorescent moiety, lysozymes by means of plaques, and phosphatase enzymes by means of chromogenic substrates such as p-nitrophenyl phosphate.

The viable signalling moiety capable of aggrandizement is adaptable to two embodiments. In the first embodiment, the signalling moiety provided is part of the analyte-signalling-entity. The signalling moiety can be the analyte moiety, the analyte-specific moiety, or another moiety attached to either the analyte moiety or the analyte-specific moiety.

In the second embodiment the signalling moiety provided is not the analyte moiety or the analyte-specific moiety, nor is it attached to the analyte moiety/analyte-specific moiety complex. The signalling moiety is provided as a separate entity. The signalling moiety is dependent on a nutrient for aggrandizement or for generation of signal. The nutrient is provided by means of a carrier such as a liposome containing the nutrient, or by means of a catalyst which generates the nutrient from a precursor. The carrier or catalyst may be either the analyte moiety, the analyte-specific moiety, or a different moiety attached to the analyte/analyte-specific moiety complex.

In the first embodiment, the signalling-analyte-entity is adaptable to four formats. In the first format, the viable signalling moiety is the analyte moiety, in the second format, the viable signalling moiety is the analyte-specific moiety, in the third format, the viable signalling moiety is a separate moiety attached directly or indirectly to the analyte moiety, and in the fourth format, the viable signalling moiety is a separate moiety attached directly or indirectly to the analyte-specific moiety.

An example of a viable signalling moiety that is also the analyte moiety is when an antibody against *Serratia marsescens* is the immobilized analyte-specific moiety and *Serratia marsescens* is the analyte moiety. Here the *Serratia marsescens* is also the viable signalling moiety capable of aggrandizement (see Example I).

An example of a viable signalling moiety that is also the analyte-specific moiety is when an IgG antibody is the immobilized analyte moiety and *Staphylococcus aureus* is the analyte-specific moiety. Here the *Staphylococcus aureus* is also the viable signalling moiety capable of aggrandizement (see Example II).

An example of a viable signalling moiety that is attached to an analyte moiety is when goat anti-rabbit IgG (Fab'2) is the immobilized analyte-specific moiety and rabbit IgG is the analyte moiety. *Staphylococcus aureus* serves as the viable signalling moiety capable of aggrandizement, and is attached directly to the analyte moiety (see Example III).

An example of a viable signalling moiety that is attached to an analyte-specific moiety is when biotinylated bovine serum albumin is the immobilized analyte moiety, avidin is the analyte-specific moiety, and *Serratia marsescens* is the viable signalling moiety capable of aggrandizement. Biotinylated antibody to *Serratia marsescens* is the bridging moiety by means of which the signalling moiety is attached to the analyte-specific moiety (see Example IV).

All the nutrients can be provided to the signalling moiety preformed, or alternatively one or more required nutrients can be provided in the form of precursors that are converted into nutrients by means of one or more catalysts. The catalyst can be part of the analyte-signalling-entity, or can be a separate unattached entity.

The method in all four formats generally comprises, but is not limited to, immobilizing either the analyte moiety or the analyte-specific moiety to a support, and treating the support so as to prevent non-specific binding to the support of any of the moieties comprising the analyte-signalling-entity. The analyte-signalling-entity is then constructed on the support by contacting the components other than the one initially immobilized with the support, either sequentially or together. The components of the analyte-signalling-entity may or may not be partially assembled before contact with the support. Components not specifically bound to the support are removed for example, by washing the support.

When a moiety other than the analyte or the analyte-specific moiety is the signalling moiety, it is attached to either the analyte moiety or the analyte-specific moiety. The attachment can be by covalent means or by non-covalent means. The signalling moiety can be attached directly to either the analyte moiety or analyte-specific moiety, or indirectly to either the analyte moiety or analyte-specific moiety by means of a signalling moiety-specific moiety and/or one or more bridging moieties. The signalling moiety can be attached to either the analyte moiety or the analyte-specific moiety before formation of the analyte moiety/analyte-specific moiety complex, or it can be attached to the analyte moiety or the analyte-specific moiety after formation of the analyte moiety/analyte-specific moiety complex. Similarly, if a bridging moiety and/or signalling moiety-specific moiety is included, it can be attached to the signalling moiety before being attached to either the analyte moiety or the analyte-specific moiety, or after its being attached to the analyte moiety or analyte-specific moiety.

Any support that can bind either the analyte moiety or the analyte-specific moiety, and any blocking agent that can prevent non-specific binding of other moieties to the support are suitable. Suitable supports include nitrocellulose, nylon membranes, glass slides, polystyrene, polypylene or polycarbonate. A preferred support is nitrocellulose, and a preferred blocking agent is bovine serum albumin (BSA). Generally, binding of the analyte moiety or the analyte-specific moiety to the support is by non-covalent means, although in some instances covalent binding is desirable.

In the second embodiment, the viable signalling moiety capable of aggrandizement is not attached to the analyte moiety/analyte-specific moiety complex. However, a catalyst or a carrier, such as a liposome, is attached to the complex. The catalyst converts a precursor into a nutrient which the signalling moiety utilizes to aggrandize or to generate a signal; the carrier contains a nutrient or nutrients required by the signalling moiety for aggrandizement or for generation of signal.

Any catalyst that can generate a nutrient without which the signalling moiety could not aggrandize or produce a particular signal is suitable for use in this embodiment, although enzymes are particularly preferred. Any precursor is suitable as long as the nutrient generated by the action of the catalyst on the precursor is utilized by the viable signalling moiety for aggrandizement or generation of signal. The nutrient can be, for example, a vitamin, an amino acid, a sugar, a coenzyme, a nucleotide, a nucleoside, a base, a fatty acid, a starch or a cofactor. Any viable signalling moiety that is auxotrophic for a nutrient can be used as a signalling moiety. Following release of the nutrient from the carrier or its generation from the precursor by means of the catalyst, the signalling moiety can aggrandize or generate a signal.

The method for forming the analyte moiety/analyte-specific moiety complex in this embodiment is similar to that described for the first embodiment. The major difference between them is in the location of the signalling moiety. In the first embodiment, the signalling moiety is attached to or is part of the analyte moiety/analyte-specific moiety complex, while in this embodiment, the signalling moiety is unattached to the analyte moiety/analyte-specific moiety complex. Aggrandizement of the signalling moiety, nevertheless, verifies the presence of the analyte moiety, because the signalling moiety cannot aggrandize or generate a signal without a particular nutrient.

An example of this embodiment uses a thymidine-requiring auxotroph of *E. coli* as the signalling moiety. An immobilized antigen which serves as the analyte moiety is detected by means of a specific antibody which has been attached to a phosphatase enzyme. The enzyme is made to cleave phosphate from thymidine 5'-monophosphate. The free thymidine is then used to supplement a thymidine-deficient growth medium which has been inoculated with the auxotrophic *E. coli*. The growth of the *E. coli* and consequent turbidity of the medium indicates the presence of the analyte moiety.

Nonviable Signalling Moieties

Non-viable signalling moieties capable of aggrandizement are moieties that can polymerize or elongate in a suitable environment. Non-viable signalling moieties include, for example, polysaccharide primers, disaccharide primers, di-, oligo-, and polynucleotide primers, conjugated dienes, alpha, beta-unsaturated carbonyl compounds, vinyl expoxides, vinyl halides, allyl halides, acrylyl chloride, and dicarboxydic acids. Particularly preferred are the polynucleotide and polysaccharide primers.

Compounds that can aggrandize the signalling moiety include all monomers, dimers and polymers that can become attached to the signalling moiety. They include, for example, deoxynucleoside triphosphates, amino acids, NTP-sugars, alkenes, alkyl or aromatic molecules containing at least one conjugated alkyl diene, alkyl or aromatic molecules containing at least one alpha, beta-unsaturated carbonyl or thiocarbonyl group, alpha, beta-unsaturated acids, alpha, beta-unsaturated carbonyl esters, amines, nitriles. Particularly preferred are the deoxynucleotide triphosphates, and NTP-sugars.

A non-viable signalling moiety is generally detected following aggrandizement. Detection can be, for example, by a formed precipitate, by a change in viscosity or refractive index of the solution, by a loss of uv absorption, or by an increase in fluorescence emmision.

Detection by formation of a precipitate or a viscous solution occurs if a polymer of sufficient length and cross-linkage is generated. Detection by a loss of uv absorption or increase in fluorescence emission occurs if the compound contains a chromophore that is lost during polymerization (e.g., a conjugated diene), or if the compound contains a fluorochrome and the number of compounds increase during polymerization. One compound can be used or several different compounds can be used. The reaction can be carried out in an aqueous solution, in an aqueous/organic solution, or in an organic solution.

The non-viable signalling moiety capable of aggrandizement is also adaptable to two embodiments. In the first embodiment, the signalling moiety is part of the analyte moiety/analyte-specific moiety complex. The signalling moiety can be the analyte moiety, the analyte-specific moiety, or another moiety attached to either the analyte moiety or the analyte-specific moiety. The presence of the analyte is thus detected by a signal derived from a signalling moiety that is either part of the analyte moiety/analyte-specific moiety complex or attached to it.

In the second embodiment, the signalling moiety is not the analyte moiety or the analyte-specific moiety, nor is it attached to the analyte moiety/analyte-specific moiety complex. The signalling moiety is provided as a catalyst that can either generate free radicals or catalyze the polymerization of a signalling moiety, or a component that can decompose to release free radicals is provided attached to the analyte moiety/analyte-specific moiety complex. The free radicals cause the aggrandizement of the non-viable signalling moiety.

In the first embodiment, the signalling-analyte-entity is adaptable to four formats. In the first format, the non-viable signalling moiety is the analyte moiety, in the second format, the non-viable signalling moiety is the analyte-specific moiety, in the third format, the non-viable signalling moiety is a separate moiety attached directly or indirectly to the analyte moiety, and in the fourth format, the signalling moiety is a separate moiety attached directly or indirectly to the analyte-specific moiety.

An example of a non-viable signalling moiety that is also the analyte moiety is when a specific polynucleotide is the analyte moiety, and a complementary polynucleotide is the analyte-specific moiety. The analyte-specific moiety is bound to a support, and its 3'-end is blocked with ATP and polynucleotide kinase.

The support is blocked to prevent non-specific binding of other moieties. The analyte moiety is contacted with the support under conditions in which specific hybrids may be formed between the complementary polynucleotides. The bound analyte moiety may be aggrandized by means of deoxynucleoside triphosphates and terminal transferase. The analyte moiety serves as a primer for the reaction. The analyte-specific moiety cannot so serve since its 3'-end is blocked. If radioactive or biotinylated deoxyribonucleoside triphosphates are provided, for example, the aggrandized analyte moiety may be readily detected.

An example of a non-viable signalling moiety that is also the analyte-specific moiety is when the analyte polynucleotide moiety is immobilized and its 3'-end blocked with a terminal phosphate. The analyte-specific moiety is then hybridized to the analyte moiety and a tail is produced on the 3'-end of the analyte-specific moiety as described above. Here the analyte-specific moiety is capable of aggrandizement. The analyte-specific moiety is aggrandized as described above for the analyte moiety. The analyte-specific moiety is not blocked in this example, and hence can serve as a primer for the reaction.

An example of a non-viable signalling moiety that is attached to an analyte moiety is when a sample suspected of containing analyte moieties (in this case, molecules of human chorionic gonadotropin) is reacted with an activated polynucleotide primer with a free 3' hydroxyl, such that all the protein moieties in the sample become attached to the polynucleotide primers. The sample is then contacted with a blocked support onto which antibody specific for human chorionic gonadotropin has been immobilized. After the non-specifically bound moieties are removed by washing, the polynucleotide primer, which is the signalling moiety, is aggrandized and detected by means of terminal transferase as described above.

An example of a non-viable signalling moiety that is attached to an analyte-specific moiety is when an antigen, the analyte moiety, is immobilized to a support, and it is complexed with an antibody, the analyte-specific moiety, that is attached to a polynucleotide primer. Here the non-viable signalling moiety capable of aggrandizement is attached to the analyte-specific moiety.

In the second embodiment, the non-viable signalling moiety capable of aggrandizement is not attached to the analyte moiety/analyte-specific moiety complex. However, if neither the analyte moiety nor the analyte-specific moiety is also a catalyst that is to be used to generate free radicals then such a catalyst is attached to the analyte moiety/analyte-specific moiety complex. The free radicals initiate the formation of a polymer by a signalling moiety. Catalysts include, for example, the peroxidase enzymes, and cofactors. Reactants from which catalysts may generate free radicals include for example, peroxides, persulfates, flavones, and azonium compounds. Examples of suitable catalysts are horseradish peroxidase enzyme, and heme co-factor. Example of components that can decompose to generate free radicals are alkyl benzoyl peroxide, and alkyl azodusobutyronitrile.

The method in this embodiment also generally comprises, but is not limited to immobilizing either the analyte moiety or the analyte-specific moiety on a suitable support. The major differences between the method of this embodiment and that of the first embodiment is that in this embodiment, the signalling moiety is not attached to the analyte moiety/analyte-specific moiety complex. The signalling moiety is any monomer that can initiate polymerization.

Aggrandizement of the signalling moiety, nevertheless verifies the presence of the analyte moiety because the signalling moiety is dependent on the presence of a catalyst or component that is attached to either the analyte moiety or the analyte-specific moiety. The catalyst generates the required free radicals to aggrandize the signalling moiety. The detection of unattached non-viable signalling moieties is similar to the detection of attached non-viable signalling moieties.

An example of this embodiment is where the horseradish peroxidase enzyme is attached to an antibody, the analyte-specific moiety, that is complexed with an antigen, the analyte moiety. The complex is then contacted with a solution containing hydrogen peroxide and polyene monomers. The horseradish peroxidase enzyme generates free radicals from the hydrogen peroxide which initiate polymerization of the polyene monomers. Detection is by formation of a plastic or gel, or by a decrease in uv absorption in the solution. Here any first monomer that begins polymerization is the aggrandizing signalling moiety.

A requirement of this invention for all embodiments is that the signalling moiety be capable of aggrandizement. However, this does not mean that the invention is limited to situations where aggrandizement is actually carried out. In certain instances the signalling moiety may be detectable without any aggrandizement at all particularly if a large amount of analyte moiety is present. In other instances some aggrandizement is necessary to permit detection. In yet other instances the signalling moiety is aggrandized until visible colonies, plaques, or polymers are formed.

The methods of this invention will often permit detection of even as little as one analyte moiety. The methods are versatile, reasonably rapid, have a simple protocol, use reagents which can be standardized and provided in commercial kits, and allow for rapid screening of a large number of samples.

Description Of Other Moieties

The analyte moiety is the entity whose presence is to be detected. The analyte moiety must have an informational portion that the analyte-specific moiety can recognize. Analyte moieties include, for example, microorganisms, fungi, algae, plant cells, animal cells, tumor cells, ligands, receptors, antibodies, antigens, proteins, hormones, polysaccharides, polypeptides, nucleic acids and polynucleotides. The analyte moiety can be derived from serum, tissue extracts, cell smears, urine, sputum, feces, saliva, puss, semen, fermentation broths, culture media, water aliquots, environmental samples, and foods.

It is recognized that experimental manipulations may be necessary to expose the informational portion of the analyte moiety to the recognition site of the analyte-specific moiety. Thus, membranes may have to be ruptured in order to obtain access to cellular components, and polynucleotides may have to be denatured to generate single-stranded regions. These methods are well known to those of ordinary skill in the art.

The analyte-specific moiety is the moiety that complexes with the analyte moiety by recognizing an informational portion of the analyte moiety. The analyte-specific moiety is thus selective for the analyte moiety. Generally, the complex is formed by hydrogen bonding, electrostatic interaction, hydrophobic interaction, or a combination of interactions. Analyte-specific moieties comprise, for example, microorganisms, ligands, receptors, antigens, antibodies, proteins, hormones, polynucleotides, amino acids, enzymes, enzyme substrates, enzyme inhibitors, and lipids.

The signalling moiety-specific moiety is a moiety that is capable of complexing to a particular signalling moiety. Its function is to attach a signalling moiety to another moiety. A bridging moiety attaches any moiety to another moiety. These moieties can be attached to the other moieties covalently or non-covalently.

Signalling moiety-specific moieties include, for example, antibodies, epitopes, antigens, receptors, polynucleotides, lectins, agglutinins, polysaccharides, coenzymes, and lipids. Bridging moieties include, for example, microorganisms, polymers, biotin, biotinylated compounds, lectins, agglutinins, avidin, antibodies, nucleic acids, proteins, lipids, saccharides, and difunctional organic compounds.

The number of moieties comprising the signalling-analyte-entity may vary. The entity may contain two moieties (analyte and analyte-specific moieties) or many moieties (analyte, analyte-specific, bridging (one or more) signalling moiety-specific, and signalling moiety). The actual number is not important for this invention.

This invention also relates to compositions comprising analyte moieties, analyte-specific moieties, and signalling moieties. Compositions are known, for example, where *Staphylococcus aureus* is attached to an antibody complexed to an antigen. However, in all these compositions, the bacteria are not capable of aggrandizement, since fixed bacteria are used. The composition disclosed in this invention, comprising a viable signalling moiety, an analyte moiety, and an analyte-specific moiety, is novel because this signalling moiety is capable of aggrandizement. The compositions further comprising a signalling moiety-specific moiety and/or bridging moiety are thus also novel.

The invention is versatile and reagents for carrying out the method can be formulated in kits. The kits would comprise, in part, the desired analyte-specific moiety, a signalling moiety, and means for attaching the signalling moiety to the analyte-specific moiety. If the analyte moiety to be detected is itself capable of aggrandizement, then the kit need not include a signalling moiety.

EXAMPLES

In the examples, reference is made to the following materials:

PBS—Phosphated buffered saline, pH 7.4.

Blocking Buffer—PBS containing 2% fetal bovine serum albumin (BSA) and 0.1% Triton X-100.

Sample Buffer—PBS containing 1% bovine serum albumin.

Nitrocellulose Membranes—Purchased from Schleicher and Scheull, Keene, N.H. BA 85 lot #4098/4.

Nutrient Agar Plates—90 mm petri plates with nutrient agar, 1.5%, containing L broth and 15 ug/ml of tetracycline.

*Serratia marsescens* —ATCC #14756, FDA strain PCI 1107. Optimum growth of this strain is at 26° C. A tetracycline-resistant variant was selected on the nutrient agar plates, and used in Examples I and III.

Rabbit antiserum directed against *S. marsescens*—Antisera were raised in New Zealand White rabbits by immunization with formalin-fixed *S. marsescens* in complete Freund's adjuvant.

*Staphylococcus aureus*—Is the protein A positive Cowan strain, tetracycline resistant.

Biotinylated Proteins—Antibody to *S. marsescens* and bovine serum albumin were reacted with NHS-$C_7$-biotin in the presence of 10% DMSO.

Avidin—Egg white avidin was purchased from Sigma Chemical Company, St. Louis, MO.

EXAMPLE I

In this example, the analyte (*S. marsescens*) was capable of aggrandizement and served as the signalling moiety.

1. Three 1 microliter samples of unmodified antiserum to *S. marsescens*, diluted 1:100 in PBS, were applied to a 4×4 cm dry nitrocellulose membrane in a triangular pattern. The membrane was permitted to air-dry.

2. The membrane was submerged in blocking buffer for 30 minutes at 37° C. in order to prevent non-specific adsorption of proteins to the membrane. 3. The membrane was washed with PBS. It was now ready for detection of *Serratia marsescens*. 4. A suspension of *Serratia marsescens* in PBS (O.D.$_{500}$ nm=0.645) was diluted 1:1000 in sample buffer. The membrane was exposed to 1 ml of the diluted suspension for 20 minutes with gentle agitation. 5. The membrane was washed 4 times in PBS in order to remove unbound organisms, and applied face-up onto the surface of a nutrient agar plate. The plate was inverted and incubated overnight at room temperature. 6. Three distinctive red colonies in the pattern of a triangle were observed, each colony corresponding to the site of application of specific antibody.

EXAMPLE II

In this example, the analyte-specific moiety (*S. aureus*) is capable of aggrandizement. The analyte moiety is IgG, to which the organism binds by means of is protein A component.

1. Three 1 microliter samples of rabbit IgG in PBS (1 mg/ml) are applied to a 4×4 cm nitrocellulose membrane in a triangular pattern. The membrane is allowed to air-dry.

2. The membrane is blocked as in Step 2 of Example I.

3. The membrane is washed 3 times with PBS. The IgG on the membrane is then detected as follows:

4. A suspension of *S. aureus* in PBS (O.D. $_{500}$ nm=1.0) is diluted 1:1000 in sample buffer. The blocked membrane is exposed to 1 ml of the diluted suspension for 20 minutes with intermittant gentle agitation.

5. The membrane is washed, applied to the surface of a nutrient agar plate and incubated overnight as described in Step 5 in Example I.

6. Colonies of *S. aureus* are observed at the site of application of the IgG.

EXAMPLE III

In this example, neither the analyte moiety (rabbit IgG) nor the analyte-specific moiety (goat anti-rabbit IgG Fab'2) is capable of aggrandizement. The signalling moiety, *S. aureus,* is attached to the analyte moiety.

1. Three 1 microliter samples of goat anti-rabbit IgG (Fab'2) in PBS are applied to a 4×4 cm nitrocellulose membrane in a triangular pattern. The membrane is allowed to air-dry.

2. The membrane is blocked as in Step 2 of Example I.

3. The membrane is washed 3 times with PBS. The rabbit IgG is detected as follows:

4. The blocked membrane is exposed to a solution of rabbit IgG in dilution buffer, 10 ug per ml for 20 minutes with intermittant gentle agitation.

5. The membrane is washed 3 times with PBS.

6. A suspension of viable *S. aureus* in PBS is prepared as in Step 4 of Example II. The membrane is exposed to the suspension as described.

7. The membrane is processed as described in Step 5 of Example II.

8. Colonies of *S. aureus* are observed at the site of application of the goat anti-rabbit IgG (Fab'2), only if the solution in Step 4 contains rabbit IgG. If no IgG is present, or if goat IgG is present, colonies are not observed.

EXAMPLE IV

In this example, neither the analyte (biotinylated bovine serum albumin) nor the analyte-specific moiety (avidin) was capable of aggrandizement. *S. marsescens* served as the signalling moiety. The latter was attached to the analyte-specific moiety by means of a bridging moiety (biotinylated antibody to *S. marsescens*).

1. Three 1 microliter samples of biotinylated bovine serum albumin (1.5 mg/ml in PBS) were applied to a 4×4 cm nitrocellulose membrane in a triangular pattern. The membrane was permitted to air-dry.

2. The membrane was blocked as in Step 2 of Example I.

3. The membrane was washed in PBS. In order to detect the biotinylated bovine serum albumin, the following procedures were performed:

4. First, the membrane was exposed to a solution of avidin (10 ug/ml in sample buffer) for 30 minutes with intermittent gentle agitation.

5. The membrane was washed 4 times with PBS to remove unbound avidin.

6. The membrane was then exposed to 1 ml of biotinylated anti-*S. marsescens* antibody, 10 ug/ml in sample buffer for 30 minutes at room temperature with intermittent gentle agitation.

7. The membrane was washed 4 times in PBS to remove unbound antibody.

8. Finally, the membrane was exposed to 1 ml of a suspension of *S. marsescens* (1:1000 dilution in sample buffer of an original suspension O.D.$_{500}$ nm = 1.0) for 30 minutes at room temperature, with intermittent gentle agitation.

9. The membrane was washed with PBS 4 times in order to remove unbound organisms. It was applied face-up onto the surface of a nutrient agar plate. The plate was inverted and incubated overnight at room temperature.

10. Three distinctive red colonies of *S. marsescens* in the pattern of a triangle were observed at the sites of application of the biotinylated BSA.

It will be apparent to those skilled in the art, that various changes, modifications, and variations may be made without departing from the spirit and scope of the invention as defined by the present claims.

What is claimed is:

1. An assay composition for detecting an analyte in a sample, which composition comprises (i) an analyte specific component capable of forming a specific complex with said anaylyte and (ii) a detectable component comprising an organism selected from the group consisting of microorganisms, fungal cells, plant cells and animal cells capable of growth or reproduction, which detectable component has been attached to said analyte specific component.

2. The composition of claim 1 wherein the detectable component is modified to be specifically bindable with said analyte.

3. The composition of claim 2 wherein said analyte specific component is specifically bindable to a macromolecule which is directly or indirectly bound to said organism.

4. The composition of claim 1 wherein said analyte specific component is covalently bound to said organism.

5. The composition of claim 1 wherein said attachment is the result of a specific binding reaction between specific binding partners, one of which specific binding partners is covalently bound to said analyte specific component and the other specific binding partner is covalently bound to said organism.

6. The composition of claim 5 wherein the specific binding partners are selected from the group consisting of avidin/biotin, avidin/iminobiotin, streptavidin/biotin, streptavidin/iminobiotin, biotin/antibiotin antibody and iminobiotin/antiiminobiotin antibody.

7. An assay method for detecting an analyte in a sample, which method comprises the steps of:
   a. affixing said sample suspected of containing said analyte to a solid support;
   b. combining said affixed analyte with a composition comprising (i) an analyte specific component capable of forming a specific complex with said analyte and (ii) a detectable component comprising an organism selected from the group consisting of microorganisms, fungal cells, plant cells and animal cells capable of growth or reproduction, which detectable component has been attached to said analyte specific component to form a resultant complex;
   c. separating non-complexed detectable component from said complex; and
   d. placing said complex in an appropriate environment to encourage growth or replication of said detectable component, wherein growth or replication is proportional to analyte concentration.

8. The method of claim 7 wherein said solid support is modified to be specifically bindable with said analyte.

* * * * *